(12) United States Patent
Bonvillain et al.

(10) Patent No.: US 12,022,823 B2
(45) Date of Patent: Jul. 2, 2024

(54) AUTOMATED BIOREACTOR SYSTEM, SYSTEM FOR AUTOMATICALLY IMPLEMENTING PROTOCOL FOR DECELLULARIZING ORGAN, AND WASTE DECONTAMINATION SYSTEM

(71) Applicant: United Therapeutics Corporation, Silver Spring, MD (US)

(72) Inventors: Ryan Bonvillain, Cary, NC (US); John Cheadle, Durham, NC (US); Thomas Petersen, Durham, NC (US)

(73) Assignee: United Therapeutics Corporation, Silver Spring, MD (US)

( * ) Notice: Subject to any disclaimer, the term of this patent is extended or adjusted under 35 U.S.C. 154(b) by 871 days.

(21) Appl. No.: 16/942,170

(22) Filed: Jul. 29, 2020

(65) Prior Publication Data

US 2020/0352157 A1 Nov. 12, 2020

Related U.S. Application Data

(62) Division of application No. 15/508,005, filed as application No. PCT/US2015/047986 on Sep. 1, 2015, now Pat. No. 10,757,932.
(Continued)

(51) Int. Cl.
*A01N 1/02* (2006.01)
*A61L 2/00* (2006.01)
(Continued)

(52) U.S. Cl.
CPC .......... *A01N 1/0247* (2013.01); *A61L 2/0017* (2013.01); *A61L 27/36* (2013.01);
(Continued)

(58) Field of Classification Search
None
See application file for complete search history.

(56) References Cited

U.S. PATENT DOCUMENTS

| | | |
|---|---|---|
| 2004/0058432 A1 | 3/2004 | Owen et al. |
| 2005/0026132 A1* | 2/2005 | Fahy .................. A01N 1/02 |
| | | 435/1.1 |

(Continued)

FOREIGN PATENT DOCUMENTS

| | | |
|---|---|---|
| CN | 1320014 A | 10/2001 |
| WO | WO-00/18226 A | 4/2000 |

(Continued)

OTHER PUBLICATIONS

Office Action dated Aug. 4, 2020 received in corresponding Japanese application No. 2017-512034, (2 pages) and English translation (4 pages).

(Continued)

*Primary Examiner* — Holly Kipouros
(74) *Attorney, Agent, or Firm* — Foley & Lardner LLP (57) ABSTRACT

An automated bioreactor system for decellularizing an organ includes a main chamber for containing the organ. The system further includes a reagent chamber containing a liquid phase reagent. A reagent conduit delivers the liquid phase reagent to the main chamber, and a perfusion conduit delivers the reagent from the reagent outlet in the main chamber into the organ. A perfusion pump drives the flow of the reagent. A perfusion pressure sensor detects a pressure of the flowing reagent. A control system controls the perfusion pump to drive the flow of the reagent based on a received input representative of a desired pressure and a received input of the detected pressure. The control system may automatically perform all of the steps of a decellularization (Continued)

protocol based on sensor input. An automated waste decontamination system may also be provided.

3 Claims, 3 Drawing Sheets

Related U.S. Application Data

(60) Provisional application No. 62/044,647, filed on Sep. 2, 2014.

(51) Int. Cl.
    *A61L 27/36*     (2006.01)
    *G01G 19/00*     (2006.01)
    *G01K 13/02*     (2021.01)
    *G01L 7/00*     (2006.01)

(52) U.S. Cl.
    CPC ............. *G01G 19/00* (2013.01); *G01K 13/02* (2013.01); *G01L 7/00* (2013.01)

(56) References Cited

U.S. PATENT DOCUMENTS

| | | |
|---|---|---|
| 2009/0202977 A1 | 8/2009 | Ott et al. |
| 2010/0093066 A1 | 4/2010 | Taylor et al. |
| 2012/0141439 A1 | 6/2012 | Ott |
| 2012/0183944 A1 | 7/2012 | Taylor et al. |
| 2013/0323708 A1* | 12/2013 | Yarmush ............... C12N 5/067 435/1.2 |
| 2014/0011182 A1* | 1/2014 | Van Sickle .......... A01N 1/0289 435/284.1 |
| 2014/0302480 A1* | 10/2014 | Ott ........................ C12M 25/14 435/1.1 |
| 2015/0342177 A1 | 12/2015 | Hassanein et al. |
| 2016/0145563 A1 | 5/2016 | Berteau et al. |
| 2018/0003944 A1 | 1/2018 | Fujii |

FOREIGN PATENT DOCUMENTS

| | | |
|---|---|---|
| WO | WO-2010/091188 A1 | 8/2010 |
| WO | WO-2011/002926 A2 | 1/2011 |
| WO | WO-2013/071096 A1 | 5/2013 |
| WO | WO-2014/110135 A | 7/2014 |

OTHER PUBLICATIONS

Office Action dated Mar. 4, 2022 in EP 15766285.9.
Price, AP et al., "Automated Decellularization of Intact, Human-Sized Lungs for Tissue Engineering," Tissue Engineering, Part C, Methods, Jun. 2014, vol. 21, No. 1, Supplementary Data Supplementary Figures S1 and S2, 2 pages.
Office Action dated Nov. 9, 2020 received in corresponding Chinese Application No. 201580059153.6 (8 pages) and English translation (9 pages).
Andrew P. Price et al: "Automated Decellularization of Intact, Human-Sized Lungs for Tissue Engineering", Tissue Engineering. Part C, Methods Dec. 2008, vol. 21, No. 1, Jun. 16, 2014 (Jun. 16, 2014), pp. 94-103, XP055232208, US.
Bonvillain R W et al: "Nonhuman primate lung decellularization and recellularization using a specialized large-organ bioreactor", JOVE (Journal of Visualized Experiments), vol. 82, Dec. 15, 2013, p. e50825, XP009187764.
Examination Report dated Nov. 26, 2018 in corresponding European application No. 15 766 285.9, 4 pages.
Final Office Action on U.S. Appl. No. 15/508,005 dated Oct. 16, 2019.
Gilpin Sarah Elizabeth et al: "Perfusion decellularization of human and porcine lungs: Bringing the matrix to clinical scale", Journal of Heart and Lung Transplantation, vol. 33, No. 3, Oct. 26, 2013 (Oct. 26, 2013), pp. 298-308, XP028616828.
International Preliminary Report on Patentability dated Mar. 16, 2017, received in corresponding International Application No. PCT/US2015/047986, 11 pages.
International Search Report in International Application No. PCT/US2015/047986 dated Mar. 9, 2016, 7 pages.
Jacques P. Guyette et al: "Perfusion decellularization of whole organs", Nature Protocols, vol. 9, No. 6, May 29, 2014 (May 29, 2014), pp. 1451-1468, XP055202257.
Non-Final Office Action on U.S. Appl. No. 15/508,005 dated Mar. 5, 2019.
Notice of Allowance on U.S. Appl. No. 15/508,005 dated Apr. 30, 2020.
Office Action dated Mar. 6, 2020 received in corresponding Chinese application No. 201580059153.6 (10 pages) and English translation (11 pages).
Office Action dated Sep. 3, 2019 received in corresponding Japanese application No. 2017-512034, (3 pages) and English translation (6 pages).
Written Opinion of the International Searching Authority in International Application No. PCT/US2015/047986 dated Mar. 9, 2016, 10 pages.

* cited by examiner

AUTOMATED BIOREACTOR SYSTEM, SYSTEM FOR AUTOMATICALLY IMPLEMENTING PROTOCOL FOR DECELLULARIZING ORGAN, AND WASTE DECONTAMINATION SYSTEM

CROSS-REFERENCE TO RELATED APPLICATIONS

This application is a divisional of U.S. patent application Ser. No. 15/508,005 filed Mar. 1, 2017, which is a U.S. National Stage of International Application No. PCT/US2015/047986 filed on Sep. 1, 2015, which claims the benefit of U.S. Provisional Patent Application No. 62/044,647, filed on Sep. 2, 2014, the entire disclosures of all of which are incorporated herein by reference.

FIELD OF THE INVENTION

The system and methods described herein generally relate to a bioreactor and its systems, and more specifically, to an automated bioreactor system for decellularizing an organ, a system for automatically implementing a protocol for decellularizing an organ, and a waste decontamination system for a bioreactor.

BACKGROUND

While allogeneic lung transplantation is the treatment for end-stage lung disease, the number of patients awaiting lung transplantation is steadily growing and only a small portion of patients receives organ transplantation because of the limited availability of donor organs. For example, chronic obstructive pulmonary disease (COPD) affects over 64 million people worldwide. The World Health Organization has predicted that by 2030 COPD will become the third leading cause of mortality. As another example, pulmonary arterial hypertension (PAH) affects the vasculature of the lungs and can result in right heart failure and death. While there are FDA-approved treatments for PAH, there are no cures, leaving lung transplantation the only option for some patients. Quite simply, there are not enough organs to meet demand.

Even in patients that receive organs available for transplantation, clinical success of lung transplantation in a patient is hampered by immunosuppression and chronic rejection, which may occur even years after the patient has undergone organ transplant. In a best case scenario, a patient holds at bay these problems by taking medications, which can come with their own serious side effects, for the remainder of the patient's life.

Tissue engineering presents an alternative to classic transplantation. This kind of regenerative approach has the potential to effectively bypass the limitations imposed by tissue donor pools and prevent allograft rejection by providing three-dimensional scaffolds for the seeding of autologous or stem cells that are specific to a particular patient. The technology involves treating an organ with a series of detergents, salts, and/or enzymes to completely remove cellular material in a process known as decellularization, while leaving the extracellular matrix intact, such that the matrix may serve as scaffold for the subsequent regeneration of tissue. Decellularization commonly involves sequential perfusion of an organ with a series of detergents and repetitive washes to remove residual DNA and other cellular debris from the organ. This can result in a scaffold in which extracellular matrix (ECM) proteins, organ architecture, and vasculature are retained. In other words, the scaffold retains the organ's structural features, but is devoid of living cells or cell components. Since cellular antigens that stimulate immune rejection are commonly found on the cell surface, removal of such antigens may reduce the risk of rejection after recellularized scaffolds are implanted into patients. For lungs, the decellularization process is particularly complex, as it requires the preservation of airways and alveoli as well as the pulmonary capillary bed to ensure the integrity of the gas exchange tissue.

Human intervention and manipulation during manually performed decellularization protocols enhance the risk of contamination, decrease consistency of the final product, and may adversely affect the three-dimensional structure and microarchitecture of the resulting scaffold, thus wasting considerable time and resources with a potentially unviable product.

SUMMARY

It is desired to provide an improved bioreactor system and systems related thereto.

One embodiment of the present invention relates to an automated bioreactor system for decellularizing an organ including a main chamber configured to contain the organ and having at least one reagent inlet, at least one reagent outlet, and at least one perfusion inlet. The system further includes at least one reagent chamber containing a liquid phase reagent and at least one reagent conduit configured to deliver the liquid phase reagent from the at least one reagent chamber to the main chamber through the at least one reagent inlet. At least one perfusion conduit is configured to deliver the liquid phase reagent from the at least one reagent outlet into the organ through the at least one perfusion inlet. At least one perfusion pump is configured to drive the flow of the liquid phase reagent through the at least one perfusion conduit. At least one perfusion pressure sensor detects a pressure of the liquid phase reagent flowing through the at least one perfusion conduit. A control system receives an input representative of a desired pressure of the liquid phase reagent flowing through the at least one perfusion conduit, receives an input of the pressure detected by the at least one perfusion pressure sensor, and outputs a signal to control the at least one perfusion pump to drive the flow of the liquid phase reagent based on the received input representative of the desired pressure and the received input of the detected pressure.

Another embodiment of the present invention relates to a system for automatically implementing a protocol for decellularizing an organ including at least one perfusion pressure sensor configured to detect a pressure of liquid flowing into the organ, at least one perfusion valve configured to control the flow of liquid into the organ, and at least one perfusion pump configured to drive the flow of liquid into the organ. The system further includes a control system configured to receive a protocol with steps for perfusing the organ, receive input from the at least one perfusion pressure sensor, and control the at least one perfusion valve and the at least one perfusion pump to automatically perform all of the steps of the protocol to decellularize the organ.

Yet another embodiment of the present invention relates to a waste decontamination system for a bioreactor including a main chamber configured to contain an organ for perfusing, a waste chamber configured to receive waste fluid from the main chamber, and a waste conduit configured to deliver the waste fluid from the main chamber to the waste chamber. The system further includes a decontamination fluid chamber configured to store decontamination fluid and a decontamination conduit configured to introduce the decontamination fluid from the decontamination fluid chamber into the waste fluid.

DETAILED DESCRIPTION

Overview

The automated bioreactor system described herein provides for a bioreactor that can be configured to perform all of the steps of a decellularization protocol automatically, with little to no user input needed for successful execution of the protocol after its initiation. The automated bioreactor system includes a main chamber where decellularization takes place and a series of reagent chambers that supply the main chamber with the reagents needed to facilitate decellularization in a continuous closed circuit. A control system, having a controller and user interface, is incorporated into the automated bioreactor system to fully automate the decellularization process in the closed system by controlling the valves and pumps that direct the flow of reagents throughout the steps of the protocol. By providing for a complete automation of the decellularization process, direct human interface with the components of the bioreactor is reduced, thereby increasing sterility, consistency, and efficiency in the process, which improves the likelihood of obtaining a more viable, and structurally sound decellularized organ for later transplantation. Moreover, the automated bioreactor system allows for a central control system capable of simultaneously performing multiple protocols across multiple bioreactors, further increasing efficiency and consistency across multiple systems.

While the processes described below are in the context of a decellularization protocol of a lung, the automated bioreactor system described herein is not limited to such a protocol or organ. For example, the automated bioreactor system may also be utilized to perform other applications for which the perfusion of an organ may be required. These applications may include, but are not limited to, processes where decellularized lungs are required as well as any downstream analyses of resulting scaffold materials, the recellularization of the scaffold, and the engineering of a nascent, functional lung. In addition, the automated bioreactor system may also be utilized to perfuse any appropriate organ or organ part. Thus, the term "organ" includes whole organs as well as any functional portions of the organ, such as a lobe of a lung.

Figure 1:
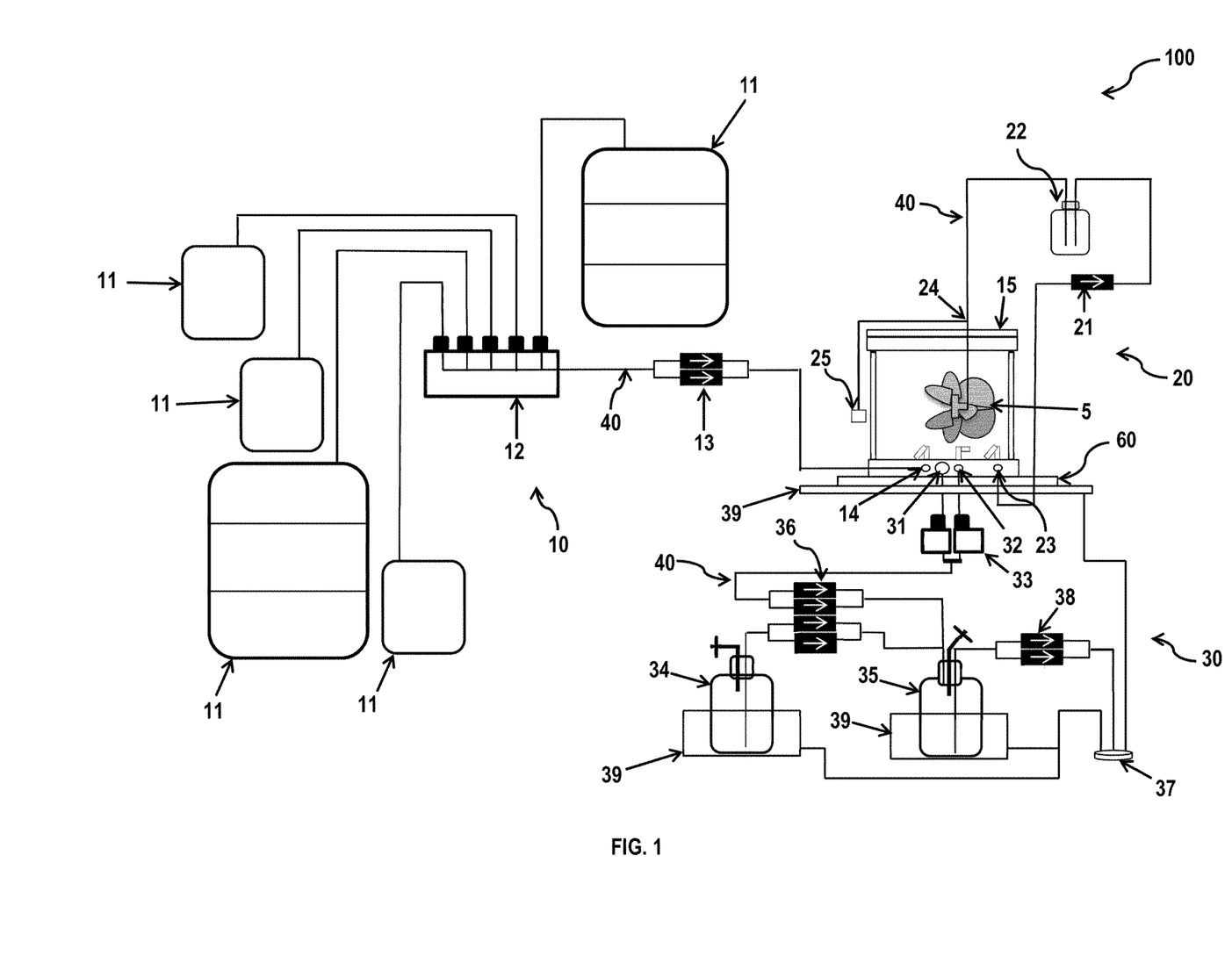
FIG. 1 is a schematic view of a bioreactor for the automated bioreactor system according to one exemplary embodiment.

FIG. 1 shows an embodiment of an automated bioreactor system 100 for performing an entire decellularization protocol of a porcine lung is shown. The automated bioreactor system 100 of FIG. 1 generally includes a main chamber 15 configured to contain a lung 5 to be perfused, a chamber fill section 10, and a perfusion section 20. A waste decontamination system 30 may also be provided for the automated bioreactor system 100.

Figure 2:
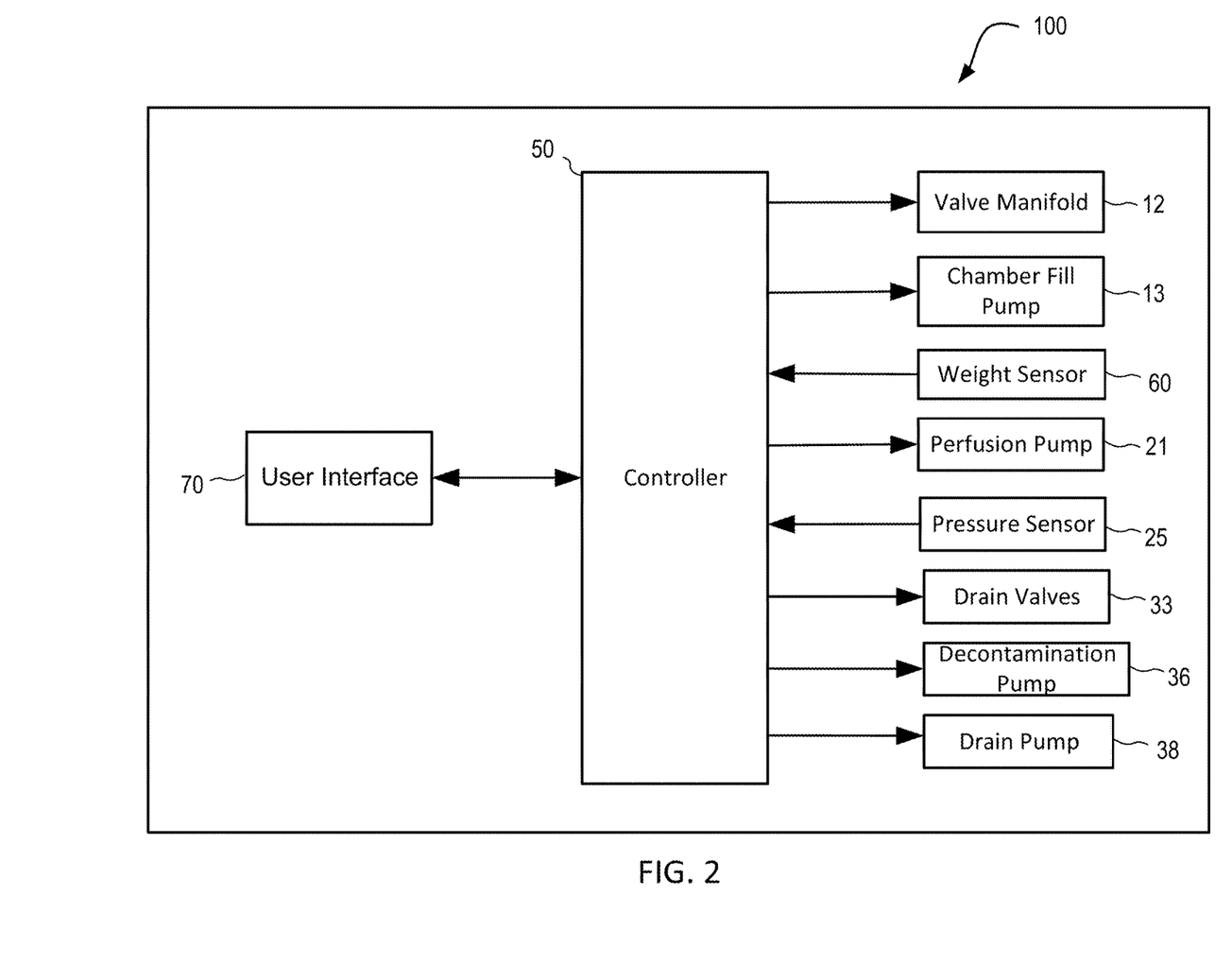
FIG. 2 is a block diagram of a control system for the bioreactor of FIG. 1 according to one exemplary embodiment.

As shown in FIG. 2, the automated bioreactor system 100 further includes a controller 50, which is electrically coupled to, and configured to control, various components within each of the sections of the bioreactor, as will be described in more detail below. In addition, a user interface 70 is further connected to and communicates with the controller 50 for user management of the automated bioreactor system 100, as will be described in more detail below.

Main Chamber

The main chamber 15 may be any appropriate chamber capable of creating and maintaining a sterile, sealed environment for the perfusion of the organ or lung 5. The main chamber 15 preferably includes a reagent inlet 14, a reagent outlet 23, a perfusion inlet 24, and waste outlets 31, 32, which are described in further detail below. In addition, the main chamber 15 is positioned on top of a weight sensor 60, which is described in further detail below. In some embodiments, at least portions of the body of the main chamber 15 are transparent or translucent, so a user can view the organ during use of the bioreactor system. In some embodiments, the main chamber 15 will have inlets for manipulation of the interior of the main chamber during use. This manipulation can occur by physically inserting objects, such as tools and instruments, into the main chamber 15 or can provide an interface for a user to manipulate objects already present in the chamber. For example, the inlets can be designed such that the main chamber 15 can be used as a glove box.

Chamber Fill Section

As shown in FIG. 1, the chamber fill section 10 preferably includes a plurality of reagent chambers 11, each fluidly connected to the main chamber 15 via a reagent conduit, which may take the form of tubing 40. While multiple reagent chambers 11 are depicted, fewer or greater numbers of chambers may be utilized. The reagent chambers 11 are configured to hold a specific type of liquid phase reagent needed for a given step in the decellularization protocol. The liquid phase reagent can be in the form of a solution, emulsion, or suspension. The reagent chambers 11 may be any suitable container to hold the reagents, such as carboys, syringes, or the like. In addition, the reagents contained in each of the reagent chambers 11 may be any suitable reagent necessary to decellularize an organ, such as phosphate-buffered saline (PBS), sodium dodecylsulfate (SDS), Triton X-100, or the like. The tubing 40 of the reagent conduit may comprise of any conventional material appropriate for the transfer of the reagents and biomaterials and for maintaining sterile connections between the chambers, such as silicon tubing or the like. As shown in FIG. 1, the reagent conduit, e.g., the tubing 40, allows the liquid phase reagents to flow into the main chamber 15 through a connection to the reagent inlet 14.

Positioned between the reagent chambers 11 and the main chamber 15 are a reagent valve manifold 12 and a reagent pump 13. The reagent valve manifold 12 controls the flow of a liquid phase reagent from a given reagent chamber 11 to the main chamber 15, which houses the lung 5. The reagent valve manifold 12 includes a plurality of valve ports. The number of valve ports provided on the reagent valve manifold 12 may be any appropriate number to allow for an in-line flow of as many liquid phase reagents as needed for the protocol. As shown in FIG. 1, the reagent valve manifold 12 includes five valve ports, allowing for the control of flow of up to five reagent chambers 11 through the tubing 40 that connects to the reagent inlet 14 of the main chamber 15. The reagent valve manifold 13 may also be any appropriate valve mechanism that can control the flow of a liquid phase reagent from a specific reagent chamber 11 to the chamber fill inlet 14 of the main chamber 15. Preferably, the reagent valve manifold 13 includes reagent valves in the form of solenoid pinch-type valve mechanisms. These solenoid pinch-type valve mechanisms can control the flow of liquid phase reagent through the tubing 40, which is flexible when using the pinch-type valve mechanism, by applying a force to the tubing 40 to impede flow of the liquid phase reagent. Such a valve mechanism is an external cut-off device, which minimizes contact with the reagents contained within the tubing 40, thereby increasing sterility of the system.

The reagent pump 13 is connected to the tubing 40 downstream to the reagent valve manifold 12. The reagent pump 13 drives the flow of a liquid phase reagent from a given reagent chamber 11 into the reagent inlet 14. The reagent pump 13 may be any appropriate mechanism for the pumping of fluid into the main chamber 15. In the embodiment shown in FIG. 1, the reagent pump 13 is a double head peristaltic pump to allow for increased flow rate and pressure, and to maintain sterility of the liquids within the tubing 40. As shown in FIG. 2, both the reagent valve manifold 12 and the reagent pump 13 are electrically coupled to, and configured to be controlled by, the controller 50.

As described above, the main chamber 15 is placed on the weight sensor 60, such as, for example, a scale. The weight sensor 60 is configured to detect a weight present in the main chamber 15. As shown in FIG. 2, the weight sensor 60 communicates a detected weight to the controller 50.

Perfusion System

An embodiment of the perfusion system 20 is shown in FIG. 1. It is preferably configured as a closed circulation system having a perfusion conduit, in the preferred form of additional tubing 40, leading from a reagent outlet 23 of the main chamber 15 to a perfusion inlet 24 of the main chamber 15, such that a liquid phase reagent contained in the main chamber 15 can be re-circulated and perfused through the lung 5. The tubing 40 forming the perfusion conduit extends further into the main chamber 15 through the perfusion inlet 24 and into the lung 5 contained in the main chamber 15. As illustrated in FIG. 1, the tubing 40 may be configured to extend into the pulmonary artery of the lung 5 such that perfusion can occur through the cardiopulmonary circuit of the lung 5.

The flow of the liquid phase reagent through the lung 5 is driven by a perfusion pump 21, which, as shown in FIG. 2, is electrically coupled to, and configured to be controlled by, the controller 50. As shown in FIG. 1, the perfusion pump 21 may be a single head peristaltic pump. A pulse dampener 22 may be included and positioned between the perfusion pump 21 and the main chamber 15. The pulse dampener 22 may serve to avoid entry of bubbles into the liquid phase reagent before perfusing into the lung 5, or may serve to prevent damage to the lung 5 caused by pulses in flow that may be generated by the perfusion pump 21 during operation. The pulse dampener 22 may be any appropriate closed container configured to hold residual fluid circulating in the perfusion system. In addition, the pulse dampener 22 may be further provided with a stir bar in order to reduce the chance of stagnation in the well of the pulse dampener 22, a condition which could lead to contamination. Furthermore, the pulse dampener 22 may allow for the reduction of noise in an output waveform of pressure in the flow of the liquid phase reagent to the lung 5. This, in turn, may allow for the pressure to be measured more accurately by a perfusion pressure sensor 25, which is described in more detail below.

Connected to the tubing 40 upstream from the perfusion inlet 24 of the main chamber 15 is a perfusion pressure sensor 25 for detecting the pressure of the liquid phase reagent flowing through the tubing 40 and into the lung 5. As shown in FIG. 2, the perfusion pressure sensor 25 is further configured to communicate a detected pressure of the liquid phase reagent with the controller 50. The perfusion pressure sensor 25 may be configured to detect a pressure of the liquid phase reagent at any point upstream from the perfusion inlet 24. As shown in FIG. 1, the perfusion pressure sensor 25 is connected to the tubing 40 such that the perfusion pressure sensor 25 detects a pressure at the perfusion inlet 24. The perfusion pressure sensor 25 may be placed outside the chamber at a height approximately matching the height at which the lung 5 floats in the main chamber 5 during perfusion.

Waste Decontamination System

As shown in FIG. 1, a preferred embodiment of the waste decontamination system 30 generally includes a decontamination fluid chamber 34 and a waste chamber 35. The waste chamber 35 is fluidly connected to receive waste fluid from the main chamber 15 via a waste conduit, which may be in the form of tubing 40, while the decontamination fluid chamber 34 is fluidly connected to the waste chamber 35 via a decontamination conduit, which may be formed by additional tubing 40. The decontamination fluid chamber 34 is configured to hold a decontamination fluid, such as, for example, bleach, while the waste chamber 35 is configured to hold a mixture containing the waste fluid from the main chamber 15 and the decontamination fluid from the decontamination fluid chamber 34.

As shown in FIG. 1, positioned between the main chamber 15 and waste chamber 35 are two drain valves 33, which control the flow of waste fluid from the main chamber 15 through waste outlets 31, 32. As described above with the valve manifold 12, the drain valves 33 may also include solenoid pinch valves as the valve-closing mechanism for enhanced sterility of the closed system. In addition, the waste outlets 31, 32 may also each be provided with a one-way valve in order to prevent the flow of waste fluid back into the main chamber 15.

Connected downstream from the drain valves 33 is a decontamination pump 36, which, as shown in FIG. 2, is electrically coupled to, and controlled by, the controller 50. The decontamination pump 36 drives the flow of waste fluid from the main chamber 10 to the waste chamber 27. In addition, the decontamination pump 36, as shown in FIG. 1, may also drive the flow of decontamination fluid from the decontamination fluid chamber 34 to the waste chamber 35. As illustrated in FIG. 1, the decontamination pump 55 may take the form of a four-head peristaltic pump, in which two pump heads are configured to drive the flow of waste fluid within the tubing 40 that connects the main chamber 15 to the waste chamber 35, and the other two pump heads are configured to drive the flow of decontamination fluid from the decontamination fluid chamber 34 to the waste chamber 35.

In some instances, certain decontamination protocols require that waste fluid be mixed with a specific proportion of decontamination fluid before the waste fluid can be safely and properly drained. For example, before disposal, waste fluid may be mixed with bleach in a desired proportion (e.g., 10%) of the total volume of the waste fluid. To achieve this, in one embodiment, the decontamination conduit leading from the decontamination fluid chamber 34 to the waste chamber 35 has a diameter that is smaller by the desired proportion (e.g., 1/10 the size) relative to the diameter of the waste conduit leading from the main chamber 15 to the waste chamber 35. And, as illustrated in FIG. 1, because the decontamination pump 36 drives the flow of both the waste fluid from the main chamber 15 and the flow of decontamination fluid from the decontamination fluid chamber 34, the decontamination pump 36 may be configured to pump at a constant flow rate such that the decontamination fluid can be mixed in a proper proportion to the rate of fluid flowing into the waste chamber 35. Moreover, as shown in FIG. 1, to ensure adequate mixing of the decontamination fluid with the waste fluid, the decontamination fluid may be introduced into the waste fluid in-line within the waste conduit and upstream from the waste chamber 35. However, the decontamination fluid may also be introduced into the waste fluid directly in the waste chamber 35 and subsequently mixed within the waste chamber 35.

In addition, separate pumps may be alternatively utilized to drive the flow of waste fluid from the main chamber 15 to the waste chamber 35 and the flow of decontamination fluid chamber 34 to the waste chamber 35. In this sense, the controller 50 may then control each of the decontamination pump 36 and the additional pump to drive the flow of waste fluid from the main chamber 10 and the decontamination fluid from the decontamination fluid chamber 34, respectively. Each of the pumps may be controlled to operate at a respective flow rate such that the decontamination fluid mixes with the waste fluid in a proportion necessary for safe and proper disposal.

As shown in FIG. 1, a drain conduit, in the form of additional tubing 40, extends from the waste chamber 35 to a drain 37. Positioned between the waste chamber 35 and the drain 37 is a drain pump 38, which drives the flow of waste fluid and decontamination fluid mixture from the waste chamber 35 to the drain 37. As shown in FIG. 2, the drain pump 38, which may be a double head peristaltic pump, is electrically connected to, and controlled by, the controller 50. Alternatively, however, the drain pump 38 may be omitted and the drain conduit may instead extend from the bottom of the waste chamber 35. A valve, such as a solenoid pinch valve, may be included downstream of an outlet of the waste chamber 35. The controller 50 may then be configured to control the valve such that, when opened, the waste fluid and decontamination fluid mixture is allowed to flow to the drain 37 via gravity.

As further shown in FIG. 1, a plurality of secondary containment chambers 39 are shown, which serve as a secondary measure to prevent waste fluid from flowing outside the automated bioreactor system 100. As illustrated in FIG. 1, the main chamber 15, the decontamination fluid chamber 34, and the waste chamber 35 are each placed in a secondary containment chamber 39. The secondary containment chambers 39 serve to hold any overflow of fluids from each of these chambers. As shown in FIG. 1, each of the secondary containment chambers 39 is connected to a plurality of drain conduits, each formed by tubing 40, which allows any fluids contained in the secondary containment chambers 39 to flow into the drain 37.

The automated bioreactor system 100 is not limited to the sensors shown in FIG. 1, and may incorporate the use of any additional sensors that may measure a variable relevant to the perfusion process. For example, a temperature control system may be included. The temperature control system may have temperature sensors placed adjacent to the main chamber 15 in order to detect a temperature of the liquid phase reagents and lung 5 contained in the main chamber 15. The temperature control system may further include a heating and/or cooling element configured to heat and/or cool the temperature of the liquid phase reagents and lung 5 contained in the main chamber 15. The temperature sensors may then be configured to communicate the detected temperature to the controller 50. The controller 50 may then be configured to control the heating and/or cooling element in order to adjust the temperature of the liquid phase reagents and lung 5 to a safe temperature for the decellularization process. By controlling for temperature within the main chamber 15, sterility of the system and the structural integrity of the organ may be further maintained. Additional sensors may also include, but are not limited to, pH sensors, conductivity sensors, and the like.

As described above, the automated bioreactor system 100 includes a bioreactor for the decellularization of a lung in a closed, sterile environment. By limiting human interaction with the mechanisms that control the decellularization process and by minimizing contact of the system's moving parts (e.g., valve mechanism, pumps) with the internal components (e.g., liquid reagents, organ), a more sterile bioreactor system may be achieved, thereby increasing the likelihood of a viable and structurally sound scaffold after the decellularization process.

Control Process

An overview of the control process for automating an entire protocol for decellularizing a lung 5 will now be described with continuing reference to FIGS. 1 and 2. In general, the control system may automatically execute all of the steps of an entire protocol by performing, sequentially and/or simultaneously, three types of processes: a chamber fill process, a perfusion process, and a waste decontamination process.

The protocol can be any of the known protocols for perfusing or decellularizing an organ, as well as being a new protocol. The protocol may be provided to the system in any of a variety of ways. For example, the protocol may be uploaded as part of a data spreadsheet. Alternatively, the protocol, or a number of protocols, may be stored on the system for selection by the user. As a further alternative, the stored protocols may be modified by the user.

The control system, or controller 50 thereof, can be a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. The steps of a method or algorithm described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such that the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal. In one or more exemplary embodiments, the functions described may be implemented in hardware, software, firmware, or any combination thereof. Such hardware, software, firmware, or any combination thereof may be part of or implemented with any one or combination of the servers, databases, associated components in the system, components thereof, and/or the like. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. In addition, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk, and Blu-Ray disc where disks usually reproduce data magnetically, while discs reproduce data optically with lasers. Combinations of the above should also be included within the scope of computer-readable media.

A chamber fill process begins with the controller 50 outputting a signal to the reagent valve manifold 12 to open one or more of the valves (while, at the same time, closing any unnecessary valves for the process) to allow for the flow of the liquid phase reagent contained in the given reagent chamber 11. At the same time, the controller 50 also outputs a signal to the reagent pump 13 to drive the flow of the liquid phase reagent(s) from the reagent chamber(s) 11 connected to the now-opened valve line(s) into the tubing 40 leading to the reagent inlet 14. The reagent pump 13 may be driven according to the protocol and/or user settings as specified. For example, the controller 50 may output to the reagent pump 13 to pump at a constant flow rate (e.g., 100 ml/min) or at a constant pressure (e.g., 30 mmHg). If the reagent pump 13 is a peristaltic pump, the controller 50 may further output to the reagent pump 13 to operate in a given direction (i.e., clockwise or counterclockwise).

As the main chamber 15 is being filled with the desired liquid phase reagent(s), the controller 50 continuously receives an input of a weight of the main chamber 15 as detected by the weight sensor 60, as shown in FIG. 2. Using this detected weight, the controller 50 then determines a volume of liquid phase reagent present in the main chamber 15 at that given time. For example, the controller 50 may determine the volume of liquid phase reagent based on both the detected weight of the main chamber 15 and a known density of the liquid phase reagent being used, which may be pre-stored in the program before execution of the protocol. By continuously monitoring the weight of the main chamber 15, and thus, the volume of liquid phase reagent present in the main chamber 15, the controller 50 may then determine when the volume of liquid phase reagent required for the chamber fill step of the protocol has been reached.

In addition, the controller 50 may also be configured to determine if and/or when a maximum volume of liquid reagent has been introduced into the main chamber 15. In this case, the controller 50 is programmed, before the execution of the protocol, with a pre-stored threshold volume that may represent the maximum volume of fluid that the main chamber 15 is capable of holding or, alternatively, some proportion of the maximum volume. During execution of a chamber fill step, if the controller 50 determines that the main chamber 10 has been filled such that the threshold volume has been reached, the controller 50 may be configured to stop the continuation of the chamber fill step (by stopping operation of the reagent pump 13) even if the chamber fill step still requires additional liquid reagent to be introduced into the main chamber 15. The controller 50 may then automatically proceed to the next step in the protocol (e.g., a perfusion step or a drain step). In this sense, by continuously monitoring the weight of the main chamber 10, the controller 50 may prevent the overfilling of the main chamber 15, thereby providing a safeguard for the system.

During a perfusion process, with all valves closed in the system, the controller 50 outputs a signal to control the perfusion pump 21 in order to drive the flow of the liquid phase reagent contained in the main chamber 15 into the lung 5 (e.g., into the pulmonary artery of the lung 5). As similarly described above with the chamber fill process, the controller 50 may output a signal to control the perfusion pump 21 in order to drive the flow of the liquid phase reagent at a constant pressure or a constant flow rate, as defined by the protocol. In addition, if a peristaltic pump is utilized, the controller 50 may direct the perfusion pump 21 to operate in a given direction as well.

During perfusion, the controller 50 continuously receives an input of a pressure of the flow of the liquid phase reagent to the lung 5 detected by the perfusion pressure sensor 25, as shown in FIG. 2. The controller 50 may be also configured to receive an input of a desired pressure and/or flow rate of the liquid phase reagent into the lung 5. The desired pressure and/or flow rate may be defined by the protocol or may be user-specified and may be inputted into the control system by an input representative of the desired pressure through the perfusion conduit. Based on the received detected pressure and the received input representative of the desired pressure, the controller 50 may then output a signal to control the perfusion pump 21 such that the desired pressure and/or flow rate into the lung 5 is continuously maintained. The controller 50 may also be configured to detect if and/or when the detected pressure has deviated by a pre-stored threshold amount from the desired pressure and/or flow rate of the liquid phase reagent into the lung 5. For example, the controller 50 may be configured to detect if and/or when the detected pressure is 15% higher or lower than the protocol-defined pressure and/or flow rate. The controller 50 may then be further configured to communicate to the user interface 70 this deviation, which may subsequently alert the user of the deviation for troubleshooting purposes.

After completion of a perfusion step, the controller 50 may be configured to initiate additional wash steps using, for example, water or saline, to rinse away residual liquid reagents from the lung 5 or the perfusion conduit before proceeding to the next step. In this case, the controller 50 may output a signal to the valve manifold 14 of the chamber fill section 10 to open the valve and allow flow from a reagent chamber 11 configured to hold a washing fluid. The controller 50 may then control the reagent pump 13 and the perfusion pump 21 to drive the flow of the washing fluid through the system.

During a waste decontamination process, the controller 50 outputs a signal to open the drain valves 33 to allow the flow of waste fluid from the main chamber 15 to the waste chamber 35. Simultaneously, the controller 50 outputs a signal to the decontamination pump 36 to direct the flow of the waste fluid from the main chamber 15 to the waste chamber 35. As described above and shown in FIG. 1, the decontamination pump 36 may be also configured to direct the flow of decontamination fluid from the decontamination fluid chamber 34 to the waste chamber 35. The controller 50 may then output a signal to the decontamination pump 36 to direct flow of both the waste fluid and the decontamination fluid through the tubing 40 such that the two fluids mix in the proper proportions. Alternatively, if two separate pumps are used to direct the flow of the waste fluid and the decontamination fluid, respectively, the controller 50 may output a signal to each of the pumps to direct a flow of the respective fluid at a rate that will ensure proper mixing of the two fluids. As similarly described above, the controller 50 may output a signal to the decontamination pump 36 to pump the waste fluid and/or decontamination fluid flowing through the tubing 40 at a constant pressure or a constant flow rate.

As the waste decontamination process proceeds, the controller 50 continuously monitors the volume of waste fluid drained from the main chamber 15 by receiving input of weight detected by the weight sensor 60. Once the required volume of waste fluid has been drained from the main chamber 15, as defined by the protocol, the controller 50 outputs a signal to the valves 33 to close. Once the waste fluid and decontamination fluid mixture has mixed and settled in the waste chamber 35 for the required amount of time to ensure adequate decontamination, the controller 50 then outputs a signal to the drain pump 38 to drive the flow of the fluid contained in the waste chamber 35 into the drain 37 for disposal. Alternatively, as described above, the controller 50 may be configured to output a signal to open a valve located at the bottom of the waste chamber such that the fluid contained in the waste chamber 35 is drained via gravity.

Figure 3:
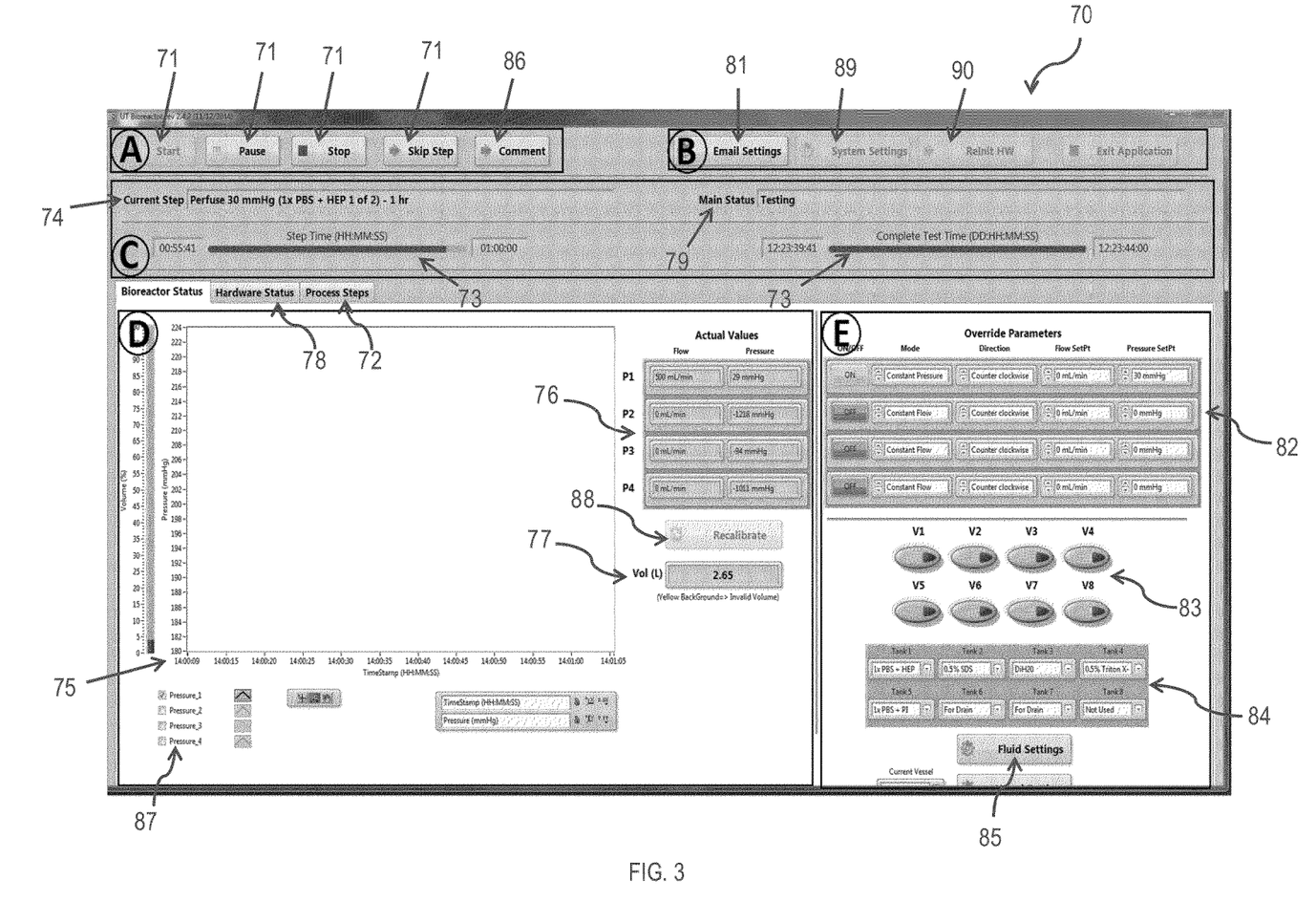
FIG. 3 is a screenshot illustrating one embodiment of a main screen of a user interface of the control system of FIG. 2.

As mentioned above, and as shown in FIG. 2, the controller 50 communicates with a user interface 70. The user interface 70 allows a user to remotely write a decellularization protocol for uploading to the control system, and then set-up and manage the automated protocol executed by the automated bioreactor system 100. An embodiment of a main screen of the user interface 70 is shown in FIG. 3 and described in further detail below.

The user interface 70 allows the user to define a series of steps (a "recipe") that contains the operating information for the pump and valve functions. The user-defined recipe serves to guide the controller 50 as to the appropriate components to control at a given time during execution of the entire protocol. The series of steps may be written by the user using any appropriate text-based program (remotely or within the user interface 70), which may then be uploaded into the control system for execution. In addition, the user-defined series of steps may be stored in the control system for later recall and execution, thereby allowing for an easy selection and execution of commonly used protocols and set-ups.

Before beginning the automatic decellularization process, the user interface 70 allows the user to set system settings of the given bioreactor being used for the decellularization protocol under a system settings command 89, which may bring up a separate window of the user interface 70 to allow the user to establish settings for the bioreactor system. Here, pressure inputs, digital outputs for the solenoid rack, and pump task may be configured here to ensure that data is read properly from the devices. Once the desired system settings have been selected by the user, the user may then begin execution of the selected protocol by the automated bioreactor system 100 through the user interface 70 via a start command. A reinitialize hardware command 90 may also be included in order to initialize the hardware before starting a new recipe.

During execution of the automatic decellularization process, the user interface 70 allows the user to remotely monitor and manage the execution of the protocol. For instance, under a section A of the main screen of the user interface 70 as shown in FIG. 3, the user may start, stop, or pause the execution of the protocol as it progresses using command buttons 71. While pausing the execution using the command button 71 temporarily stops all pumps, the user can still turn on the pumps by using the override parameters contained in section E, which is described in further detail below. In addition, the command buttons 71 may further includes a skip command, allowing the user to skip a current step in the protocol and proceed to a subsequent step.

The user interface 70 may also provide the user with real-time information regarding the status of the bioreactor as the protocol is executed. For example, as shown in FIG. 3 under section C, the user interface 70 may allow the user to view the time remaining in the execution of the current step and/or overall protocol under indicators 73. The user interface 70 may also provide a viewable list of all the steps of the protocol under a tab 72 and indicate the current step being executed by the system under an indicator 74. In addition, the user interface 70 may allow the user to monitor the input received by the controller 50 from the various sensors present in the system. For example, the user interface 70 may be configured to display a waveform chart 75 showing pressure as detected by the pressure sensor 25 over time under section D of the main screen shown in FIG. 3. Aspects of the waveform chart may be manipulated by the user with appropriate graphical manipulation tools (e.g., zoom, scale, drag, etc.). Actual, measured values of the pressure and flow rate determined by the controller 50 based on the detected pressure input received from the pressure sensor 25 may also be displayed via a table 76. Moreover, for systems utilizing multiple pressure sensors, a toggle button 87 may be provided such that the user can switch and/or add real-time information regarding the pressures detected by each of the pressure sensors. Similarly, the volume of liquid phase reagent contained in the main chamber 15 as determined by the controller 50 may also be displayed in real-time through an indicator 77 under section D. The user may zero and/or calibrate any pressure sensors utilizing a recalibrate command 88. However, preferably the recalibrate command 88 is only active before a recipe is started and becomes inactive while an automated decellularization protocol is active.

In addition, the user interface 70 may also be configured to inform the user of the current operating states of the valves and pumps. For example, the user interface 70 may indicate to the user the current operating status of a given pump (e.g., idle, testing, alarm state) under a tab 78. Under this tab, errors for the pressure inputs, the pumps, and the solenoids may be displayed. Scale debug values may also be displayed, which include measurements for volume display and are used to calculate the volumes for the fill steps.

The overall main status of the system (e.g., idle, testing/running, alarm state) may be indicated to the user through an indicator 79 under section C of the main screen of the user interface 70. As described above, the controller 50 may be configured to detect if a detected pressure of a flow rate driven by a given pump deviates by more than a predetermined threshold. If such deviation occurs, the controller 50 may then communicate this status to the user interface 70, which may be configured to alert the user of the alarm state of the pump (e.g., indicator 79 changes from green to yellow when the pressure reading deviates by 15% from the pressure set point of at least one pump, then from yellow to red when the pressure reading deviates by more than 30% from the pressure set point of at least one pump).

To allow for troubleshooting, the user interface 70 may contain override parameters under section E of the main screen as shown in FIG. 3. In this section, the user can alter pump settings and valve status during execution of the protocol in order to deviate from the uploaded protocol. For example, pump settings may be overridden via a pump control section 82. Using the pump control section 82, the user may turn a pump on or off, change the mode of operation of the pump (e.g., constant flow rate to constant pressure), change the direction of operation of the pump (e.g., clockwise to counterclockwise), and/or change the flow rate and/or pressure set point. Similarly, the valve settings may also be changed under a valve control section 83, in which the user may open or close a specific valve in the system. Fluid settings may also be manually changed via a fluid control section 84. As shown in FIG. 3, the user may select a fluid from a bank of drop-down menus, which correspond to the fluid flow controlled by the valves shown in valve control section 83. Alternatively, the user may choose to manually insert a specific fluid not contained in the drop-down menu and, thus, may utilize a fluid settings command 85 to update the system. Once selections are updated, the density information may then be passed to the control system for calculation of the display volume and target fill volume of the main chamber 15. A vessel settings command may also be included to allow the user to enter information about the bioreactor themselves. Thus, the user interface 70 allows for continuous monitoring and management of the automatic decellularization process in order to allow for a more effective and efficient control of the overall protocol.

The user interface 70 may also include a notification settings command 81 that allows the user to remotely receive notifications regarding the system as it executes the protocol. This settings command 81 may allow for automatic notification, in the form of, for example, email, of any changes in a given step by the control system and periodic updates on the state of the system as a whole. In addition, the user interface 70 may allow for the insertion of time-stamped comments to the data log via a comment command 86, which is saved in the system for later viewing. This may allow the user to note specific changes made to the protocol for analysis purposes, such as inserting indicating notes about steps taken during the set-up that might correspond to abnormalities in the data log, for example, by adjusting a pressure sensor.

The user interface 70 may also allow for the monitoring and management of the execution of a plurality of protocols, each being executed within a separate bioreactor, such as the one shown in FIG. 1. In this case, the controller 50 acts as a central control system and controls the components of each of the bioreactors according to each of the user-defined series of steps. The user interface 70 may allow the user to toggle between executed protocols in order to monitor and manage each separate protocol simultaneously. By allowing for such a centralized system, several decellularization protocols may be performed simultaneously, thereby increasing efficiency of the entire process.

Exemplary Protocol for the Preparation of Lung Tissue to be Decellularized by a Bioreactor System A clean work area is prepared in a biological safety cabinet (BSC). All steps of the preparation procedure are performed using good aseptic technique to minimize introduction of environmental microbial contaminants. Sterile sleeves and gloves and exchange gloves are used as needed.

The pluck (i.e., the heart-lung circuit) is unpacked from the shipping container and critically examined for trauma to the vasculature, airway, pleura, and parenchyma. The pluck can then be appropriately dissected under sterile conditions. The packaging can be sterilized. The pulmonary artery cannula is inserted into the pulmonary artery and secured, and the pluck is dissected such that the heart muscle is removed. Any remaining heart tissue may be trimmed away. The lung may then be perfused via the pulmonary veins with heparinized saline for anticoagulation during subsequent perfusion in the bioreactor system. The prepared lung is then weighed and transferred to a laminar flow hood area for loading into the main chamber when required.

Exemplary Setup of the Bioreactor in the Laminar Flow Hood

With the laminar flow hood blower on, the laminar flow hood is sprayed down with the appropriate cleaning solution. The autoclaved main chamber is brought near the laminar flow hood, and the outer layer of autoclave wrap is unwrapped. The main chamber is slid into the hood using a ramp. With sleeves and surgical gloves, the inner layer of the autoclave wrap on the main chamber is unwrapped and removed from the hood. Spacers between the bioreactor glass and the base are removed. Once all spacers are removed, it is verified that the glass is sitting on the bottom gasket with an even margin around the base.

The autoclave wrap that covers the glass is removed. A person outside the laminar flow hood removes the outer layer of the top ring, and brings it into the hood using sterile gloves. A sterile drape is brought into the hood. The top ring is then secured to the metal standoffs using bolts and tools.

The main chamber lid is brought into the laminar flow hood. The lid is placed on top of the main chamber, and fasteners attach the lid to the top ring. Now that the main chamber is closed to the environment, all of the ports on the lid and the base are tightened. Using the biowelder, the reagent conduit line is welded to the reagent tubing assembly. The assembly is welded to a reagent chamber. Using a peristaltic pump, the main chamber is filled.

After filling to the level of the tube drain, the reagent pump is stopped. The perfusion conduit is welded from the base to one end of the pulse dampener. The other side of the pulse dampener is welded to the perfusion conduit at the top of the bioreactor, completing the perfusion circuit.

Perfusion is started by perfusing solution through the perfusion conduit, and air is removed from the lines using a sterile syringe. The main chamber is filled to approximately 20 L.

Exemplary Protocol for the Aseptic Installation of the Lung in the Laminar Flow Hood The perfusion pump is run slowly (25 mL/min) and all air is purged in the perfusion conduit. The organ (lung) is brought to the laminar flow hood in a draped sterile pan. The cranks on the main chamber lid are loosened. With sterile gloves, the lung is moved into the main chamber and the connection(s) are made.

The perfusion conduit is assessed for any air bubbles. Using the reagent pump, solution is pumped backwards into the 1×PBS reagent chamber until the main chamber is at about 20 L. The reagent conduit is sealed and disconnected from the 1×PBS reagent chamber. The main chamber is then removed from the laminar flow hood and transferred to the decellularization station. The laminar flow hood is disinfected after installation of the lung with the appropriate disinfectant.

Exemplary Automated Lung Decellularization Protocol

Once the main chamber is placed atop the scale, a biowelder is used to weld the following lines and complete the bioreactor fluid circuit: (1) reagent conduit; (2) drain conduit; (3) reagent chamber connections to the valve manifold.

Perfusion is then started manually at a low rate. About 1-2 L of PBS is manually filled into the main chamber at 1000 mL/min speed.

The perfusion pressure sensor is placed outside the chamber at a height of 40 L, matching the height at which the lung will be floating for the majority of the experiment. The perfusion pressure sensor is zeroed by pressing the "Recalibrate" button, then pressure transducer 1 (or whichever transducer is controlling the perfusion pump, specified by the recipe) is zeroed.

The experiment is initiated by pressing the "Start" button, following the prompts for the appropriate recipe file, data save location, and solution/chamber settings.

A sample automated decellularization process to which a lung set might be exposed is as follows: (1) perfuse PBS at 30 mmHg for 2 hours once recipe is initiated drain 20 L from the main chamber; (2) perform five cycles of chamber fill, perfusion, and drain over five days of 0.5% SDS; (3) perform one cycle of chamber fill and drain and one day of exposure of $DiH_2O$; (4) perform one cycle of chamber fill, perfusion, and drain over one day of 0.5% Triton-X; and (5) perform five cycles of chamber fill, perfusion, and drain over five days of PBS of final wash steps.

Frequent monitoring of the tissue state and bioreactor function is important to this process; manual intervention for overflow waste draining may be required depending on tissue perfusion efficiency. Sampling of chamber fluids may be undertaken during the process for sterility testing or analytics. These samples are taken through the swabbable port on the top of the main chamber.

Exemplary Storage of the Decellularized Tissue

At the end of the experiment, the decellularized tissue will either be stored, sampled and formalin-fixed, or both.

The experiment is stopped on the software interface by pressing the "stop" button. The main chamber is drained manually (drain waste first, if necessary) until no liquid remains in the main chamber. Using a clipster tool or a heat seal tool, all connections from the main chamber to the peripheral tubing are closed off.

Prior to putting the main chamber into the laminar flow hood, the exterior of the main chamber is disinfected. The main chamber is loaded into the laminar flow hood, then the sterile pan/drape. The lid is removed. Using sterile gloves, the lung is disconnected from the perfusion conduit and brought into the pan. The pan is removed from the laminar flow hood and brought into a biosafety cabinet for storage or sampling. The main chamber is removed from the laminar flow hood, and the unit is disinfected according to protocol.

Exemplary Protocol for Chamber and Station Cleaning

All tubing and fittings downstream of the chamber (drain conduit, waste) should be disposed of in a biohazard waste container. Perfusion conduit tubing should be disposed of in this manner as well; however the pressure sensors can be cleaned and saved.

Due to the coating on the main chamber and relative fragility of its components, main chamber parts must be washed by hand with a mild detergent. Clean main chamber parts are allowed to dry.

The waste chamber is stripped of its external tubing—this tubing is disposed of as biohazard waste. The carboys themselves can be washed in the parts washer. The cap/dip tube in the waste drain carboys should be washed by hand. The overfill protection containers that house the waste drain carboys can be washed by hand if there was a spill during the decellularization experiment. The bleach carboys need not be washed just filled up again with bleach when appropriate. The bleach line tubing circuit should be replaced each decellularization to avoid cracking of the fittings that are exposed to bleach.

The residual fluid in the pulse dampener should be decontaminated with bleach and poured down the drain. The pulse dampener itself may be disassembled and washed. The stir bar may be washed by hand or in the basket in the parts washer.

Exemplary Operation of the Bioreactor Program

The bioreactor program is opened from the computer desktop and system settings are updated if a hardware or software change has occurred. Under System Settings, the following four properties must be set for a normal decellularization process in order to ensure that data will be read properly from the devices: (1) analog input device (pressure inputs); (2) DigOut device (solenoids); (3) analog output task (pump control); and (4) scale COM port (scale-port connection). Flow rate limits, which determine the minimum and maximum flow rate in the perfusion line when the perfusion pump is pressure-controlled are also set. The PC ID is used as an identifier to which system parameters are saved. For example, when the PC ID is set to "bioreactor 1", all the associated settings are saved to this ID. The PC ID (and associated system settings) that was last used in execution of the program will appear by default upon subsequent executions of the program. The PID parameters default to a value of 0.1 for Kp, Ki, and Kd. The median filter rank is a filter which averages the data points read from the pressure sensor to minimize noise. The larger the value specified, the larger the observed filter effect. It defaults to a value of 2, but can be modified to reduce the noise in the pressure chart. A value of 25 has been found to suitable for the automated decellularization process.

The "Email Setting" button will open the Email Configuration screen. Email settings can be changed at any time. A box is checked to receive email messages, which include notification of system status changes and periodic test status emails. The interval at which emails will be received is entered. For example, specifying an interval of 01:00:00 will send periodic emails every hour. Periodic emails are sent as a verification of the current status of the system, steps, pumps, and solenoid valves. Additionally, system status change emails will be sent whenever the system status changes, whether by automatic or manual operation. After all information is appropriately inputted, a test email is sent by clicking a "Test" button. If the settings are satisfactory and the test email has been received, the "Save and Exit" button is pressed to save changes and return to the main screen.

By clicking the "Start" button, a Select Recipe box is brought up. The most recent recipe text file is opened by clicking on the "Open .XLS File" button. Recipe files are generally located on a desktop folder. The recipe is reviewed to ensure that the proper file was selected, and a "Continue" Button is clicked which prompts the user to enter data logging information. A folder is chosen in which to save the data. The folder chosen should reflect the bioreactor station used (4A, 4C, 5A, 5C). Data point save frequency (60 seconds) is selected. The "Continue" button is selected once all settings have been entered to start the process.

Upon selecting the recipe, the user will be asked to validate that the fluid and vessel settings as appropriate. After selecting the recipe, the user will be prompted one final time before starting the automated decellularization process. Once started, the recipe can be paused by clicking the 'Pause' button on the front panel. A user may need to pause execution of the recipe for troubleshooting purposes. In a paused state, the program will display a flashing "Resume" button, which prompts the user to continue the execution after manual troubleshooting. In a paused state, a user may toggle valves, turn pumps on and off, and adjust pump settings. Though pumps may be running during a paused state, the background color will remain gray, indicative of an idle state. Data continues to be recorded even in a paused state. The recipe resumes in the same step and with the same remaining step time at which it was paused. If any pump settings were changed during pause, these changes will persist upon resuming the step. Pumps and the solenoid valves can be manually set while the recipe is running A user may need to manually adjust these settings for troubleshooting purposes, such as switching the perfusion pump to constant pressure instead of constant flow. The override settings will persist for the remainder of the step, as well as through a pause and resume action.

Once the recipe has completed the final step, the main status will display "Test Completed". Data is logged to a file, which can be accessed via Microsoft Excel. Pressure vs. Timestamp data for the duration of the execution is stored.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention.

Unless otherwise specified, "a" or "an" means "one or more."

All of the publications, patent applications and patents cited in this specification are incorporated herein by reference in their entirety.

What is claimed is:

1. A system for automatically implementing a protocol for decellularizing an organ, comprising:
   a main chamber configured to contain the organ;
   at least one perfusion pressure sensor configured to detect a pressure of liquid flowing into the organ;
   a weight sensor configured to detect a weight contained in the main chamber;
   at least one perfusion pump configured to drive the flow of liquid into the organ; and
   a control system configured to:
      receive a protocol with steps for perfusing the organ;
      receive input from the at least one perfusion pressure sensor; and
      control the at least one perfusion pump to automatically perform all of the steps of the protocol to decellularize the organ;
   wherein the control system is further configured to:
      receive an input of the weight detected by the weight sensor; and
      stop a completion of a step of the protocol and proceed to performing a subsequent step of the protocol based on the received input of the detected weight.

2. The system of claim 1, wherein the control system is further configured to receive an input from a user during the protocol to allow a user to override a step of the protocol and to adjust a setting of the at least one perfusion pump.

3. The system of claim 1, wherein the control system is further configured to store the protocol and recall the protocol upon a request of a user.

* * * * *